United States Patent
Takaki

(10) Patent No.: US 7,871,699 B2
(45) Date of Patent: Jan. 18, 2011

(54) IODINE-CONTAINING HOT MELT PRESSURE SENSITIVE ADHESIVE CAPABLE OF BEING MELTED AND COATED AT A TEMPERATURE NOT HIGHER THAN 100C, AND A MEDICAL ADHESIVE SHEET PRODUCT WITH SUCH A PRESSURE SENSITIVE ADHESIVE

(75) Inventor: Shunsuke Takaki, Sagamihara (JP)

(73) Assignee: 3M Innovative Properties Company, St. Paul, MN (US)

( * ) Notice: Subject to any disclaimer, the term of this patent is extended or adjusted under 35 U.S.C. 154(b) by 328 days.

(21) Appl. No.: 11/596,151

(22) PCT Filed: May 6, 2005

(86) PCT No.: PCT/US2005/015829

§ 371 (c)(1),
(2), (4) Date: Dec. 6, 2007

(87) PCT Pub. No.: WO2005/113029

PCT Pub. Date: Dec. 1, 2005

(65) Prior Publication Data

US 2008/0193706 A1 Aug. 14, 2008

(30) Foreign Application Priority Data

May 12, 2004 (JP) ............... 2004-142280

(51) Int. Cl.
*A61L 15/58* (2006.01)
*B32B 25/04* (2006.01)
*B32B 25/14* (2006.01)

(52) U.S. Cl. ............... 428/355 R; 428/355 EN; 428/355 BL; 523/122

(58) Field of Classification Search .................. None
See application file for complete search history.

(56) References Cited

U.S. PATENT DOCUMENTS

| | | | |
|---|---|---|---|
| 2,550,622 A * | 4/1951 | Taub ........................ 424/671 |
| 4,310,509 A | 1/1982 | Berglund et al. |
| 4,638,797 A * | 1/1987 | Merrill et al. ................ 602/52 |
| 4,814,168 A * | 3/1989 | Sablotsky et al. ........... 514/182 |
| 4,990,144 A * | 2/1991 | Blott ........................ 604/304 |
| 5,012,801 A | 5/1991 | Feret |
| 5,013,785 A * | 5/1991 | Mizui ........................ 524/490 |
| 5,069,907 A | 12/1991 | Mixon et al. |
| 5,270,358 A | 12/1993 | Asmus |
| 5,322,695 A | 6/1994 | Shah et al. ................... 424/448 |
| 5,369,155 A | 11/1994 | Asmus |
| 5,607,699 A * | 3/1997 | Hoang et al. ................. 424/672 |
| 5,635,203 A * | 6/1997 | Gale et al. ................... 424/448 |
| 5,650,215 A | 7/1997 | Mazurek et al. |
| 5,670,557 A | 9/1997 | Dietz et al. |
| 5,674,561 A | 10/1997 | Dietz et al. |
| 5,779,632 A | 7/1998 | Dietz et al. |
| 5,803,086 A | 9/1998 | Scholz et al. |
| 5,829,442 A | 11/1998 | Cox et al. .................... 128/849 |
| 5,853,750 A | 12/1998 | Dietz et al. |
| 5,952,398 A | 9/1999 | Dietz et al. |
| 5,979,450 A | 11/1999 | Baker et al. |
| 6,143,317 A | 11/2000 | Himmelsbach et al. |
| 6,216,699 B1 | 4/2001 | Cox et al. |
| 6,566,575 B1 | 5/2003 | Stickels et al. |
| 6,723,337 B1 * | 4/2004 | Song et al. ................... 424/448 |
| 6,939,936 B2 | 9/2005 | Wang et al. |
| 7,189,793 B2 | 3/2007 | Wang et al. |
| 2002/0098349 A1 * | 7/2002 | Watanabe et al. ............ 428/343 |
| 2003/0165560 A1 | 9/2003 | Otsuka et al. |
| 2003/0212176 A1 * | 11/2003 | Wang et al. .................. 524/402 |
| 2007/0142494 A1 | 6/2007 | Kalgutkar et al. |

FOREIGN PATENT DOCUMENTS

| | | |
|---|---|---|
| EP | 0272149 | 6/1988 |
| EP | 0528191 | 2/1993 |
| JP | 08-056982 | 5/1996 |
| JP | 09-176021 | 8/1997 |
| WO | WO 95/20634 | 8/1995 |
| WO | WO 97/05171 | 2/1997 |
| WO | WO 00/56828 | 9/2000 |
| WO | WO 00/78885 | 12/2000 |
| WO | WO 02/072162 | 9/2002 |
| WO | WO 03/091354 | 11/2003 |

* cited by examiner

*Primary Examiner*—Jennifer C McNeil
*Assistant Examiner*—Adam C Krupicka

(57) ABSTRACT

An object of the invention is to provide an iodine-containing hot melt pressure sensitive adhesive that can be melted and coated at a temperature not higher than 100° C., and that can retain stability of the iodine in the adhesive through all stages of making, storage and use thereof, without utilizing any harmful organic solvent, while utilizing the antimicrobial efficacy of iodine.

14 Claims, No Drawings

IODINE-CONTAINING HOT MELT PRESSURE SENSITIVE ADHESIVE CAPABLE OF BEING MELTED AND COATED AT A TEMPERATURE NOT HIGHER THAN 100C, AND A MEDICAL ADHESIVE SHEET PRODUCT WITH SUCH A PRESSURE SENSITIVE ADHESIVE

CROSS REFERENCE TO RELATED APPLICATIONS

This application is a national stage filing under 35 U.S.C. 371 of PCT/US2005/015829 filed May 6, 2005, which claims priority to Japanese Patent Application No. 2004-142280, filed May 12, 2004, the disclosures of which are incorporated by reference in their entirety herein.

TECHNICAL FIELD

The invention relates to a hot melt pressure sensitive adhesive, and more particularly relates to a hot melt pressure sensitive adhesive that contains iodine and that can be melted and coated at a temperature not higher than 100° C., and also relates to a medical adhesive sheet product, such as a surgical drape, surgical tape, wound dressing or the like, with such a pressure sensitive adhesive.

BACKGROUND

During surgical operation, human skin (a natural barrier against microorganisms) is cut through at a predetermined operating site, and internal tissues which should be aseptic by nature are then exposed to the external environment. This greatly increases the risk of a surgical site infection (SSI). Therefore, the skin at and around the operating site must be disinfected to reduce the number of microorganisms existing there to the smallest possible number. Even after disinfection, the microorganisms remaining on the skin may cause an infection during the surgical operation. In order to minimize potential of infection, a sterilized surgical drape that is made of a transparent, thin adhesive film is generally used, which may be called as "surgical drape for incision" or "incise drape". The incise drape is adhered and affixed onto the skin around the operating site prior to the operation, and allows the skin together with the drape to be incised by means of a surgical knife or the like, to aid in preventing any microorganism remaining on the skin at and around the incised site from invading inside of the body through the incised site. After a surgical operation, the wound is typically covered with a thin and flexible film, which may be called a "wound dressing", in order to create an optimized environment for healing while obviating any infection from the external environment.

There are known dressing films and surgical drapes made with iodine-containing pressure sensitive adhesives for use in antimicrobial medical applications, as described in U.S. Pat. No. 4,310,509; U.S. Pat. No. 5,829,442 and the like. However, these pressure sensitive adhesives are dissolved or dispersed in an organic solvent such as toluene, methyl ethyl ketone or the like. Such a solvent-based pressure sensitive adhesive may have adverse affects on the human body and the environment, as well as having certain cost and process issues. Therefore, there is a need for an iodine-containing pressure sensitive adhesive that does not utilize organic solvents which may adversely affect the human body and/or the environment, and a process of making the same.

As iodine has a tendency to easily sublime as well as having a boiling point of 106° C., it is difficult to make a hot melt pressure adhesive containing iodine, and coat the adhesive using a typical hot melt coater of which coating temperature is over 110° C. In order to obtain a hot melt pressure adhesive capable of being coated by a typical hot melt coater (typically at a coating temperature of about 140 to 160° C.), a hot melt pressure adhesive composition has been developed, which comprises an antimicrobial agent diiodomethyl-p-tolylsulfone which is stable at a temperature of 275 to 350° F. (135 to 177° C.) so as to enable the adhesive composition to be coated using the hot melt coater. However, it has been found that this antimicrobial agent has a different antimicrobial spectrum and a poor antimicrobial efficacy, as compared to iodine ($I_2$, or polyvinyl pyrrolidone-iodine complex (also referred to simply as "PVP-iodine complex")).

SUMMARY

The iodine ($I_2$ or PVP-iodine complex) is a very effective antimicrobial agent, exhibiting antimicrobial activity against a wide spectrum of microorganisms, including Gram-negative bacteria; Gram-positive bacteria; tubercule bacillus; fungi; viruses; and certain spore forming bacteria. The antimicrobial efficacy of iodine is well known and widely accepted by healthcare professionals. Therefore, an iodine-containing pressure sensitive adhesive is desired that is capable of being melted and coated, with minimizing loss of iodine at a higher temperature to the minimum, while still utilizing such an antimicrobial efficacy of iodine.

One object of the present invention is to provide an iodine-containing hot melt pressure sensitive adhesive that can be melted and coated at a temperature not higher than 100° C., and that can stably preserve the iodine in the adhesive through all the stages of making, storing and using it, without utilizing any harmful organic solvent, while utilizing the well known and widely used antimicrobial efficacy of iodine.

The present invention relates to an iodine-containing hot melt pressure sensitive adhesive composition that is capable of being melted and coated at a temperature not higher than 100° C., comprising:
  (a) an iodine-containing hydrophilic gel, comprising
    (i) polyvinyl pyrrolidone-iodine complex, and
    (ii) a hydrophilic solvent capable of dissolving polyvinyl pyrrolidone therein;
  (b) a hot melt pressure adhesive base having a softening point of not higher than 100° C., comprising
    (i) 15 to 30% by weight of a synthetic rubber consisting of a saturated type thermoplastic elastomer,
    (ii) 20 to 35% by weight of a tackifier that is non-reactive with iodine, and
    (iii) 35 to 50% by weight of a plasticizer that is non-reactive with iodine, based on the total weight of the hot melt pressure adhesive base; and
  (c) a surfactant.

The present invention also relates to a medical adhesive sheet product, comprising:
  (a) a sheet substrate; and
  (b) an iodine-containing hot melt pressure sensitive adhesive composition as described according to the present invention, coated on the sheet substrate.

DETAILED DESCRIPTION

Since the iodine-containing hot melt pressure sensitive adhesive composition of the present invention can be melted and coated at a temperature not higher than 100° C., it can suppress any loss of iodine due to its sublimation to the minimum. Also, since the iodine-containing hot melt pressure sensitive adhesive composition of the invention has low levels of ingredients that contains any ethylenically unsaturated bond or acetylenically unsaturated bond, any degradation of adhesive and any loss of iodine due to its reaction with the adhesive can be avoided. Further, the iodine-containing hot melt pressure sensitive adhesive composition of the invention can remain stable by retaining iodine in the adhesive, since the iodine-containing hydrophilic gel and the hot melt pressure sensitive adhesive base are homogeneously dispersed by addition of a surfactant and they are stable without any phase separation. Thus, the iodine-containing hot melt pressure sensitive adhesive composition of the invention can preserve iodine in the adhesive through all the stages of making, storing and use it. Furthermore, the iodine-containing hot melt pressure sensitive adhesive composition of the invention is advantageous also in that it preferably uses a non-ionic surfactant that has low skin irritating potential, as well as low levels of organic solvent (e.g. less than 5 wt %) that may be harmful to the human body and the environment.

The medical adhesive sheet product made with the aforesaid iodine-containing hot melt adhesive composition of the present invention can remain stable by retaining iodine in the adhesive through both the stages of making and storing it, and can suppress iodine sublimation to the minimum, even after stored for a long period of time. Further, since the iodine-containing hot melt pressure sensitive adhesive composition of the invention can be softened and coated at a temperature not higher than 100° C., it is advantageous also in that it can be coated directly on the sheet substrate while minimizing heat damage in making the medical adhesive sheet product.

The present invention relates to a hot melt pressure sensitive adhesive that contains iodine and that can be melted and coated at a temperature not higher than 100° C., and that does not utilize any harmful organic solvent, and also relates to a medical adhesive sheet product coated with such a pressure sensitive adhesive.

Conventionally and commonly used hot melt pressure sensitive adhesives are those which are melted and coated by a hot melt coater of which temperature is typically at about 140 to 160° C. Iodine has a tendency to easily sublime even at room temperature, and it intensively sublimes above its melting point, 114° C. If the melting and coating temperatures of a hot melt adhesive containing iodine are above 100° C., iodine would easily sublime and an undesirable loss of iodine would result in a decrease in the antimicrobial efficacy of the adhesive.

Iodine is also very highly reactive, and may be easily reacted with unsaturated functional groups, above all with ethylenically unsaturated bonds (>C=C<) and acetylenically unsaturated bonds (—C≡C—). For example, acrylic pressure sensitive adhesives may include residual monomers containing ethylenically unsaturated bonds. During compounding the acrylic adhesives with iodine in an extruder, the iodine may easily react with ethylenically unsaturated bonds of the residual monomers. This may lead to not only loss of iodine due to its reaction, but also cross-linking in the adhesive. This may result in a problem that the adhesive, when compounded with iodine in the extruder, is cured and hardened so that the adhesive becomes difficult to be extruded, as well as a problem of insufficient antimicrobial efficacy of the iodine-containing adhesive.

In addition, iodine in the presence of moisture can form hydrogen iodide HI. The acid is corrosive, and it may cause corrosion on the extruder and other equipments.

In order to prevent the aforesaid problems, an iodine-containing hot melt pressure sensitive adhesive for use in antimicrobial medical applications, preferably satisfies the following requirements:
 i) The adhesive preferably is melted or softened at a temperature not higher than 100° C., preferably between 70 and 90° C., in order to prevent any loss of iodine contained therein due to its sublimation. Such a low temperature process is advantageous also in that it can dilute the level of HI formed and the extent of attack of any HI that is formed.
 ii) The adhesive remains stable by retaining the iodine in the adhesive, through all the stages of making, storing and using it.
 iii) The materials used in the adhesive should preferably be a combination of substances that are non-reactive with iodine. As used herein, the term "non-reactive with iodine" is intended to mean that the ingredient of the adhesive does not react with iodine contained in the adhesive, under a normal condition where the adhesive is made, stored and used (particularly, under atmospheric pressure and at a temperature lower than or equal to 100° C.), and more particularly means that the ingredient of the adhesive is essentially free of any ethylenically unsaturated bond or acetylenically unsaturated bond that may be easily reacted with iodine. The term "essentially free" as used herein is intended to mean that such species containing ethylenically unsaturated or acetylenically unsaturated bonds are typically present at less than 5% by weight, more preferably at less than 3% by weight, and most preferably at less than 1% by weight.

The iodine-containing hot melt pressure sensitive adhesive composition of the present invention satisfies the above requirements. Among hot melt pressure sensitive adhesives, the pressure sensitive adhesive of the invention is particularly directed to one that is capable of being melted and coated at a temperature not higher than 100° C. For convenience in explanation, the hot melt pressure sensitive adhesive that is capable of being melted and coated at a temperature not higher than 100° C., is hereinafter referred to as "warm melt pressure sensitive adhesive" or simply as "warm melt adhesive". Also, the hot melt pressure sensitive adhesive that contains iodine and that is capable of being melted and coated at a temperature not higher than 100° C., is hereinafter referred to as "iodine-containing warm melt pressure sensitive adhesive" or simply as "iodine-containing warm melt adhesive". The iodine-containing warm melt pressure sensitive adhesive composition of the present invention will be described in detail and for more specified aspects.

A. Warm Melt Pressure Sensitive Adhesive Base

The warm melt pressure sensitive adhesive base, needs to be softened at a temperature not higher than 100° C., as is referred to as "warm melt" adhesive. Further, each ingredient of the warm melt adhesive base is a material that is essentially free of ethylenically unsaturated bonds nor acetylenically unsaturated bonds, and non-reactive with iodine. The warm melt pressure sensitive adhesive base, suitable to meet these requirements, comprises: (i) a synthetic rubber consisting of a saturated-type thermoplastic elastomer, (ii) a tackifier that is non reactive with iodine, and (iii) a plasticizer that is non reactive with iodine, and optionally, (iv) one or more additives that are nonreactive with iodine.

Preferably, the synthetic rubber consisting of the saturated type thermoplastic elastomer is essentially free of ethylenically or acetylenically unsaturated bonds, and is non-reactive with iodine. Preferred examples of the saturated type thermoplastic elastomer are hydrogenated styrene based thermoplastic elastomers ("hydrogenated SBC"). The hydrogenated styrene based thermoplastic elastomers include hydrogenated styrene-butadiene-styrene block copolymers ("hydrogenated SBS"), hydrogenated styrene-isoprene-styrene block copolymers ("hydrogenated SIS"), hydrogenated styrene-ethylene-styrene block copolymers ("hydrogenated SES"), hydrogenated styrene-ethylene/butylene-styrene block copolymers ("hydrogenated SEBS"), hydrogenated styrene-ethylene/propylene-styrene block copolymers ("hydrogenated SEPS"), polymer alloys thereof, and blends thereof. Preferably, the elastomer used in the warm melt adhesive base is selected from hydrogenated styrene-ethylene/butylene-styrene block copolymers ("hydrogenated SEBS"), hydrogenated styrene-ethylene/propylene-styrene block copolymers ("hydrogenated SEPS"), polymer alloys thereof, and blends thereof.

The synthetic rubber by itself is generally difficult to form a pressure sensitive adhesive due to its weak adhesion. Therefore, one or more tackifiers and one or more plasticizers, and optionally, one or more other additive components are compounded with the rubber component.

The tackifier is preferably selected from a material that is essentially free of any ethylenically or acetylenically unsaturated bonds, and is non-reactive with iodine. The tackifier includes, but is not limited to, hydrogenated rosin resins, hydrogenated and esterified rosin resins, hydrogenated terpene resins, aliphatic (preferably C5 based) petroleum resins, aromatic (preferably C9 based) petroleum resins, alicyclic petroleum resins obtained by hydrogenating aromatic petroleum resins, and the like. Preferably, the tackifier used is selected from aliphatic (C5 based) petroleum resins, particularly C5 based liquid hydrocarbon resins.

Similarly, the plasticizer is selected from a material that is essentially free of any ethylenically or acetylenically unsaturated bonds, and is non reactive with iodine. The plasticizer includes, but is not limited to, mineral oils, phthalic acid esters, glycol esters, hydrocarbon plasticizers (e.g. polybutene, polyisobutylene, oligomers of ethylene/propylene), and the like. Among them, the plasticizer used is preferably a material, such as mineral oil, that can dissolve the rubber component therein and can be stable when stored.

If desired, any known additives used in known hot melt pressure sensitive adhesives, such as antioxidants, ultraviolet absorbers, fillers, and anti-aging agents, may be incorporated into the warm melt adhesive base. However, they should be selected from materials that are essentially free of any ethylenically unsaturated bonds or acetylenically unsaturated bonds and are non-reactive with iodine.

In order to form a warm melt pressure sensitive adhesive base that is capable of being melted and coated at a temperature not higher than 100° C., the ratio of the components being compounded is important. It is determined, in part on desired properties for the adhesive base, such as its softening temperature, coating temperature, adhesive force to skin, change in adhesive force over adhesion time, etc. Generally, a higher level of plasticizer contained in an adhesive tends to lower the softening temperature of the adhesive, while a higher level of tackifier tends to give a higher tack and a higher adhesive force to the skin. A typical formulation to provide a warm melt adhesive base that is capable of being melted and coated and that gives a sufficient adhesive force is at least 15 wt. % thermoplastic elastomer; at least 20 wt. % plasticizer; and at least 35 wt. % tackifier, based on the total weight of the warm melt adhesive base. A typical formulation to provide a warm melt adhesive base that is capable of being melted and coated and that gives a sufficient adhesive force is no more than 30 wt % thermoplastic elastomer; no more than 35 wt % plasticizer; and no more than 50 wt % tackifier, based on the total weight of the warm melt adhesive base.

The warm melt pressure sensitive adhesive base may be prepared by mixing the components according to any of usual procedures, or any of commercially available warm melt pressure sensitive adhesives may be used for the warm melt pressure sensitive adhesive base. Commercially available warm melt adhesives include, for example, Ecomelt® series supplied from Collano AG, Switzerland, including: Ecomelt® M1-186 (softening point: 77° C.), M1-193 (softening point: 84° C.), M1-328 (softening point: 88° C.), M1-340 (softening point: 93° C.), and the like. The softening point is measured according to ASTM D36/E28.

B. Methods for Stabilizing Iodine in Pressure Sensitive Adhesive

As iodine has a tendency to easily sublime even at room temperature, it is required that iodine is stably preserved in the pressure sensitive adhesive, through all of the stages of making, using and storing the iodine-containing warm melt pressure sensitive adhesive and the stage of storing a medical adhesive sheet product made with the iodine-containing warm melt pressure sensitive adhesive. The iodine-containing hydrophilic gel of the present invention has been developed to provide the retention of iodine in a pressure sensitive adhesive, as described below.

(1) Iodine as Simple Substance in Warm Melt Pressure Sensitive Adhesive

Because iodine as simple substance is dissolved in a mineral oil, it can be dissolved into the mineral oil ingredient of a warm melt pressure sensitive adhesive as described in above section A, to form a warm melt pressure sensitive adhesive having iodine homogeneously dissolved therein. Such an iodine-containing warm melt pressure sensitive adhesive can be melted and coated at a temperature not higher than 100° C. However, it has been found that the iodine dissolved in the adhesive tends to sublime easily and in a large quantity while it is stored in a moisture barrier bag over a long period of time.

(2) Warm Melt Pressure Sensitive Adhesive+PVP-Iodine Complex

As an approach for stable fixation of iodine, utilization of polyvinyl pyrrolidone-iodine complex (PVP-iodine complex) is well known and widely used. PVP-iodine complex can be mixed with a warm melt pressure sensitive adhesive as described in above section A, by a standard mixing means (e.g. planetary mixer) controlled at a predetermined temperature. While iodine of the PVP-iodine complex was dissolved in the mineral oil ingredient of the adhesive, PVP powder of the same was, however, dispersed in a nonhomogenous manner in the warm melt pressure sensitive adhesive, but not dissolved in any ingredient of the adhesive, as will be described in a referential example below. Thus, by mixing PVP-iodine complex with a warm melt pressure sensitive adhesive is eventually comparable to dissolving iodine in a warm melt pressure sensitive adhesive, and it may not be able to preserve iodine in the adhesive for a long period.

(3) (PVP-Iodine Complex in Hydrophilic Solvent)+Warm Melt Pressure Sensitive Adhesive The PVP-iodine complex can be dissolved in a certain hydrophilic solvent to form a homogeneous hydrophilic gel. The hydrophilic gel formed of PVP-iodine complex and hydrophilic solvent can be mixed with a warm melt pressure sensitive adhesive as described above, by a standard mixing means (e.g. planetary mixer) controlled at a predetermined temperature. However, the hydrophilic gel is easily separated from the warm melt pressure sensitive adhesive, as will be described in a referential example below. Thus, by mixing PVP-iodine complex dissolved in the hydrophilic solvent with a warm melt pressure sensitive adhesive, it may not be able to obtain a homogeneous and stable iodine-containing warm melt pressure sensitive adhesive composition.

(4) (PVP-Iodine Complex in Hydrophilic Solvent)+Surfactant+Warm Melt Pressure Sensitive Adhesive As will be described in the examples below, by utilizing a certain surfactant, the iodine-containing hydrophilic gel formed of PVP-iodine complex and hydrophilic solvent can be homogeneously dispersed in the warm melt pressure sensitive adhesive, as a W/O (water in oil)-type emulsion. The resulting iodine-containing warm melt pressure sensitive adhesive composition is homogeneous and stable, and can be melted and coated at a temperature not higher than 100° C. Further, in the iodine-containing warm melt adhesive composition and in a medical adhesive sheet product made with the same, iodine can be stably retained in the adhesive composition. During storage, sublimation of iodine can be suppressed in a moisture barrier bag, and even after stored for a long period, there will be only a small quantity of iodine sublimation.

(5) (PVP-Iodine Complex+Iodide in Hydrophilic Solvent)+Surfactant+Warm Melt Pressure Sensitive Adhesive As will be described in working examples below, by further adding a certain iodide salt to the iodine-containing hydrophilic gel formed of PVP-iodine complex and hydrophilic solvent, iodine stability can be improved in the pressure sensitive adhesive composition (W/O type emulsion). By the addition of iodide salt in the resulting iodine-containing warm melt adhesive composition and in a medical adhesive sheet product made with the same, sublimation of iodine can be significantly suppressed in a moisture barrier bag during storing them, and even after stored a long period, there will be little or no iodine sublimation.

C. Hydrophilic Solvent

For use in forming the iodine-containing hydrophilic gel as described in above section B, an appropriate hydrophilic solvent is a solvent that is capable of dissolving polyvinyl pyrrolidone (PVP) therein. For example, the international publication WO03/091354 describes examples of various types of "solubilizing liquids" or "plasticizers", including the following: (1) water; (2) C1-C10 alcohols such as ethanol, isopropanol, n-propanol, phenoxyethanol and butanol; (3) C3-C6 ketones such as acetone and methylethylketone; (4) C2-C8 esters such as methyl acetate, ethyl acetate and butyl acetate; (5) C2-C8 ethers such as tetrahydrofuran; (6) amides such as N-methylpyrrolidone; (7) lactones such as butyrolactone; (8) aromatic organic solvents such as toluene and xylene; (9) compounds containing one or more hydroxyl groups, and particularly glycols such as glycerin; 1,2-pentanediol; 2,4-diethyl-1,5-pentanediol; 2-methyl-1,3-propanediol; as well as monofunctional compounds such as 3-methoxy-methylbutanol (MMB); (10) polyethoxylated phenols such as Pycal 94 (phenoxypolyethyleneglycol); (11) alkyl, aryl, and aralkyl ether glycols such as those sold under the Downol tradename by Dow Chemical, such as propylene glycolmono-n-butyl ether (Dowanol® PnB), tripropylene glycolmono-n-butyl ether (Dowanol® TPnB), dipropylene glycol mono-n-butyl ether (Dowanol® DPnB), propylene glycol monophenyl ether (Dowanol® PPH), propylene glycol monomethyl ether (Dowanol® PM); (12) polyethoxylated alkyl phenols such as Triton® X35 and Triton® X102; (13) mono or polysubstituted polyethylene glycols such as PEG 400 diethylhexanoate (TegMer 809, CP Hall), PEG 400 monolaurate (CPH-30N, CP Hall) and PEG 400 monooleate (CPH-41N, CP Hall); (14) amides such as higher alkyl substituted N-alkyl pyrrolidones such as N-octylpyrrolidone; (15) sulfonamides such as N-butylbenzene sulfonamide (CP Hall); (16) benzoate esters such as those available from Velsicol Chemical Corp., under the Benzoflex tradename including dipropylene glycoldibenzoate (Benzoflex® 50), diethylene glycol dibenzoate, benzoic acid diester of 2,2,4-trimethyl-1,3-pentane diol (Benzoflex® 354), ethylene glycol dibenzoate, tetraethylene glycol dibenzoate, and the like; (17) polyethylene glycols and ethylene oxide/propylene oxide random and block copolymers having a molecular weight of less than 10,000 daltons, preferably less than about 5000 daltons, more preferably less than about 2500 daltons; (18) polyalkylene glycols such as polypropylene glycol, polytetramethylene glycol, or random or block copolymers of C2-C4 alkylene oxide; and the like. Any of these compounds may be used in the present invention. As used herein the term polyethylene glycols refer to glycols having 2-6 hydroxyl groups, that are derived from ethylene glycol, propylene glycol, glycerin, trimethylolpropane, pentaerythritol, sucrose or the like, and that have been reacted with ethylene oxide or a 2-haloethanol.

Further, for use in medical applications, it is preferred that a solvent that is harmless to the human body and the environment and that has low skin-irritating potential is used. Such a PVP-dissolving hydrophilic solvent includes a solvent that contains only a hydroxyl group or groups as its functional group, including: water; monohydric alcohols such as methanol, ethanol and propanol; dihydric alcohols such as ethylene glycol, polyethylene glycols (PEGs) and propylene glycol; trihydric alcohols such as glycerin; and the like, and a mixture of two or more of these solvents may be used. Among them, glycols such as polyethylene glycols (PEGs), for example PEG100 to PEG600, and glycerin are particularly preferred, in terms of stabilizing the W/O type emulsion being formed from hydrophilic gel and warm melt adhesive base. Most useful hydrophilic solvents are PEG300 and glycerin.

D. Surfactant

Surfactants may be classified into: cationic surfactants; anionic surfactants; and non-ionic surfactants. Any type of surfactants may be used in the present invention. As a surfactant for use in medical applications, a non-ionic surfactant is desired, because it has low skin-irritating potential. The non-ionic surfactants include: (1) sorbitan ester-type surfactants, such as those sold by ICI Co. as Span® and Tween® series; (2) polyethoxylated surfactants, such as those sold as Triton® X35 and Triton® X102; (3) fatty acid monoesters of polyethylene glycol, such as polyethylene glycol 400 monolaurate and polyethylene glycol 400 monooleate; and the like.

Among various types of non-ionic surfactants, sorbitan ester-type surfactants are suitable to form a homogeneous dispersion from the iodine-containing hydrophilic gel and the warm melt adhesive base, as described in above section B. The sorbitan ester-type surfactants include, but not limited to, sorbitan fatty acid esters (including mono-, di- and tri-fatty acid esters of sorbitan and); ethylene oxide (EO) adducts of sorbitan fatty acid esters; and the like. Examples of commercially available sorbitan fatty acid ester surfactants include Span® series supplied from ICI Co., such as Span® 20 (sorbitan monolaurate), Span® 40 (sorbitan monopalmitate), Span® 60 (sorbitan monostearate), Span® 65 (sorbitan tristearate), Span® 80 (sorbitan monooleate), Span® 85 (sorbitan trioleate), and the like. Examples of commercially available EO adducts of sorbitan fatty acid esters include Tween® series supplied from ICI Co., such as Tween® 20 (EO adduct of sorbitan monolaurate), Tween® 40 (EO adduct of sorbitan monopalmitate), Tween® 60 (EO adduct of sorbitan monostearate), Tween® 65 (EO adduct of sorbitan tristearate), Tween® 80 (EO adduct of sorbitan monooleate), Tween® 85 (EO adduct of sorbitan trioleate), and the like.

Among them, preferred for the present invention are sorbitan fatty acid esters, such as Span® series. Particularly, Span® 20 (sorbitan monolaurate) is the most preferable surfactant, because it can not only homogeneously dissolve the iodine-containing hydrophilic gel in the warm melt adhesive base, but also form a transparent dispersion even at room temperature.

The amount of surfactant added will influence the stability of the hydrophilic gel and the adhesive force. Excessive amounts of surfactant tend to make the resulting adhesive composition wet and weaken its adhesive force. On the other hand, too little surfactant tends to easily cause phase separation, and affect stability of the adhesive composition. The amount of surfactant added is preferably at least 0.1% by weight, and most preferably at least 0.3% by weight, based on the total weight of the iodine-containing warm melt adhesive composition. The amount of surfactant added is preferably no more than 5% by weight, and most preferably no more than 0.5% by weight, based on the total weight of the iodine-containing warm melt adhesive composition.

E. Iodide Salt

The iodine-containing warm melt pressure sensitive adhesive composition of the invention may optionally comprise an iodide salt in order to improve the suppression of iodine sublimation within a moisture barrier bag during storing the adhesive composition, as described in above section B. The iodide salt as used herein includes sodium iodide, potassium iodide and other iodide salts that are soluble in the aforesaid hydrophilic solvent (such as glycols, glycerin and the like).

F. Making of Iodine Containing Warm Melt Pressure Sensitive Adhesive Composition The iodine-containing warm melt pressure sensitive adhesive composition of the invention can be made by adding powder PVP-iodine complex and optionally an iodine salt, to a hydrophilic solvent that is capable of dissolving PVP therein, and mixing them to be homogeneous; adding a surfactant to the mixture and mixing them to form a homogeneous iodine-containing hydrophilic gel; and mixing a warm melt pressure sensitive adhesive base with the iodine-containing hydrophilic gel, by a standard mixing means (e.g. planetary mixer) at a temperature of 70 to 100° C., preferably between 80 to 95° C. The iodine-containing warm melt pressure sensitive adhesive obtained in this process is homogenous, and causes no phase separation or curing, when stored at room temperature, and after once cooled, it can be re-melted without any significant change. Thus, the iodine-containing warm melt adhesive composition according to the invention is stable at the stages of making and storing the same.

G. Coating of Iodine-Containing Warm Melt Pressure Sensitive Adhesive Composition The iodine-containing warm melt pressure sensitive adhesive composition of the invention can be melted and coated by a standard hot melt coater equipped with an extruder, at a temperature not higher than 100° C., preferably at a temperature between 70 to 90° C., with no or little loss of iodine. The iodine-containing warm melt adhesive composition will remain stable without causing any phase separation, any degradation or any loss of iodine in the extruder, and can be re-melted without any degradation in the coating head. Thus, the iodine-containing warm melt adhesive composition according to the invention is stable at the stage of using the same.

H. Applications of Iodine Containing Warm Melt Pressure Sensitive Adhesive Composition The iodine-containing warm melt pressure sensitive adhesive composition of the invention can be used in a wide variety of applications where it is desired to utilize the antimicrobial efficacy of iodine. Such applications of the iodine-containing warm melt adhesive composition include, but are not limited to, medical, skin and beauty applications. The iodine-containing warm melt composition of the invention is particularly useful for a medical adhesive sheet or adhesive tape product (herein referred to generically as "medical adhesive sheet product"). The medical adhesive sheet product made with the iodine-containing warm melt adhesive composition of the invention is advantageous in that iodine can be preserved in the adhesive composition, and sublimation of iodine can be almost completely suppressed during storing the same. The medical adhesive sheet product includes, but not limited to, surgical drapes such as incise drapes or surgical drapes for incision, surgical tapes, wound dressings, adhesive tapes and the like.

The iodine-containing warm melt adhesive having coating temperature not higher than 100° C. according to the invention, is advantageous in that it can be coated on a sheet substrate while minimizing heat damage of the sheet substrate. Particularly, when it is used to make a thin medical adhesive sheet product such as surgical drape for incision, it can be directly applied on a certain thin elastic film such as polyurethane elastomer film or polyester elastomer film.

I. Sterilization of Medical Adhesive Sheet Product

Any medical adhesive sheet product such as surgical drape for incision is usually sterilized before use. One appropriate method for sterilizing a medical adhesive sheet product made with the iodine-containing warm melt adhesive composition of the invention is by irradiation with Gamma-ray, typically over 10 KGy, preferably over 20 KGy, and more preferably over 25 KGy, to a sealed package containing the medical adhesive sheet product.

J. Adhesion of Warm Melt Pressure Sensitive Adhesive Composition

After irradiation with Gamma-ray, there may be an increase in adhesive force of the pressure sensitive adhesive coated on the medical adhesive sheet product. Therefore, the level of initial adhesive force desired for a pressure sensitive adhesive should be determined, with this phenomenon taken into consideration. An appropriate level of initial adhesive force for a pressure sensitive adhesive to be applied to the human skin is in the range of 100 g/inch to 500 g/inch. A preferable level of initial adhesive force level, in order to obtain a reliable adhesive force that is sufficient to secure the adhesive sheet to the skin against any detachment during operation, is in the range of 150 g/inch to 350 g/inch. After the operation, too high a level of adhesive strength is undesirable in order to protect the skin against any damage at the time of peeling the medical adhesive sheet product from the skin. A preferable level of adhesive strength at the time of peeling after the operation is in the range of 100 g/inch to 200 g/inch.

K. Sheet Substrate

For a sheet substrate onto which the iodine-containing warm melt pressure sensitive adhesive composition of the invention is coated, any sheet may be used of which dimension and material are those usually used in the art for an intended medical adhesive sheet product. The sheet substrate usually used for a medical adhesive sheet product is, typically, an elastic film such as polyurethane elastomer film, polyester elastomer film or the like. The sheet substrate may be a porous film or a non-porous film. However, it is preferred to use a porous and moisture vapor permeable sheet substrate, in order to prevent any lowering of adhesive force of the adhesive due to inefficiency of letting out the moisture vapors transpired from the skin. In general, such a moisture vapor permeable sheet substrate has a moisture vapor transmission rate (MVTR) of greater than 500 g/m²/24 h.

L. Imparting Moisture Vapor Permeability

The iodine-containing warm melt pressure sensitive adhesive of the invention has a moisture vapor transmission rate (MVTR) (<about 100 g/m²/24 h) which is much lower than that of the moisture vapor permeable sheet substrate as described above. Accordingly, even with a moisture vapor permeable sheet substrate, lowering of adhesive force of the adhesive may occur due to inefficiency of letting out the moisture vapors transpired from the skin, unless the adhesive layer has an improved MVTR. In order to prevent any occurrence of such lowering of adhesive force of the adhesive, the medical adhesive sheet product (i.e. sheet substrate on which the iodine-containing pressure sensitive adhesive has been coated), according to the present invention, preferably has a MVTR of greater than about 100 g/m²/24 h, and more preferably, a MVTR of greater than about 500 g/m²/24 h. In order to make a medical adhesive sheet product having such a level of MVTR, improvement in MVTR of the medical adhesive sheet product can be achieved by forming one or more holes, preferably a number of holes, only through the adhesive layer, by means of embossing (preferred embodiment), heat needling or the like, on the adhesive layer. This should not result in any hole formed extending through the sheet substrate such as elastic film, and the sheet substrate as a barrier against microorganisms should not be broken. The hole diameter and hole density to be formed on the adhesive layer, depend on what level of MVTR is desired, and a person ordinarily skilled in the art will easily determine them, based on the disclosure of this application. The embossing on the adhesive layer can be carried out with an embossing roll, at a temperature in the range of room temperature to 100° C., preferably in the range of room temperature to 90° C.

The following examples are given to illustrate the present invention and are not intended to limit the scope of the invention. Unless explicitly indicated otherwise, all parts and percentages are given by weight.

EXAMPLES

Comparative Example

Iodine-Containing Warm Melt Adhesive

1% iodine-containing warm melt pressure sensitive adhesive Ecomelt® M1-225, commercially available from Collano AG, was provided. The Ecomelt® M1-225 is an adhesive with 1 weight % of iodine added to Ecomelt® M1-186 (softening point: 77° C.). The hot melt pressure sensitive adhesive base is comprised of a hydrogenated SEBS rubber, a hydrocarbon resin, a mineral oil and other additives. The pressure sensitive adhesive base can be melted at a temperature not higher than 100° C., and has a warm melt property. The iodine can be dissolved into the mineral oil ingredient of the adhesive, and can be preserved at room temperature.

Making and Sterilization of Incise Drape:

In order to make an incise drape, a 25 μm-thick polyester elastic film Hytrel® 4056 (from Dupont Co.) and a 50 μm-thick polyester liner with a silicone release coating were provided. By using a hot melt hand held coater of which temperature was set to a temperature of 90 to 100° C., the 1% iodine-containing warm melt adhesive Ecomelt® M1-225 was coated on the aforesaid polyester liner. The coating gap was 50 μm. The iodine-containing warm melt adhesive layer coated on the polyester liner, was then laminated with the aforesaid polyester elastic film to form an incise drape.

The incise drape having the iodine-containing warm melt adhesive layer coated thereon was placed into a package bag with aluminum foil-type moisture barrier pouch. The package bag was then heat-sealed. The package pouch containing the incise drape therein was then sterilized by irradiation with Gamma-ray over 25 KGy.

Performances of Incise Drape:

The sterilized incise drape having the iodine-containing warm melt adhesive layer coated thereon, was tested and evaluated on performances as follows: thickness of the coated adhesive layer, iodine content, skin adhesive force, iodine sublimation, deformation of the coated adhesive layer, and bleeding of adhesive. The skin adhesive force was measured in 180° peel adhesion test at the pulling rate 30 cm/min, according to JIS-Z0237, which is generally used for pressure sensitive adhesives to skin application. The iodine content was analyzed in an X-ray fluorescent spectrometer. The iodine sublimation was determined by visual inspection.

The tests of these performance were conducted on the incise drape, both at the initial state immediately after the Gamma-ray irradiation, and at the state after accelerated aging testing of 9 weeks at 49° C. or 18 weeks at 49° C., which corresponds to one year or two years aging, respectively, in accordance with the Von't Hoff theory employed in the Food and Drug Administration (FDA) Guidance. The Accelerated Aging Time Duration ("AATD") can be estimated, with Accelerated Aging Rate ("AAR"), from the Von't Hoff equations as follows:

AATD=(Desired Real Time Aging)/AAR

AAR=$Q_{10}$[((Test Temperature)−(Ambient Temperature))/10]

Where: $Q_{10}$=2.0,

Ambient temperature=22° C.

Test temperature=49° C.

Table 1 shows the results of performances of the incise drape using the iodine-containing warm melt pressure sensitive adhesive Ecomelt® M1-225.

TABLE 1

Performances of Incise Drape with Adhesive Ecomelt ® M1-225

| M1-225 Adhesive | Initial State | After Aging 1 year |
|---|---|---|
| Condition | G-ray 25GKy | 9 Weeks @ 49° C. |
| Thickness (micron) | 40 | 40 |
| Adhesion (g/inch) | 100 | 142 |
| Iodine Content (mg/cm²) | 0.047 | 0.040 |
| Iodine Sublimation On Hytrel ® Film | None | Significant |
| Iodine Sublimation Inside Pouch | None | Significant |
| Adhesive Layer Deformation | None | Patterned |
| Bleeding of Adhesive | None | None |

The incise drape exhibited good performances at its initial state. However, after 9 weeks at 49° C. of accelerated aging test corresponding to 1 year aging, it was found that much iodine had sublimed from the adhesive, and adhered to inside the moisture barrier pouch and on the Hytrel® film. Iodine was unstable in this type of adhesive, and it was found difficult to use for making an incise drape with an iodine-containing pressure sensitive adhesive.

Referential Example 1

Warm Melt Adhesive+PVP-Iodine Complex

In this example, use of polyvinyl pyrrolidone-iodine complex is studied, in order to stably fix iodine in the adhesive.

A non-iodine containing Ecomelt® M1-186 (softening point: 77° C.) from Collano AG was used as warm melt pressure sensitive adhesive. It was attempted to mix powdery PVP-iodine complex (from Aldrich Co., iodine content: 11.6%) with the warm melt pressure sensitive adhesive, in a standard planetary mixer of which temperature was controlled at a temperature of 85 to 95° C. Although iodine of the PVP-iodine complex was dissolved into the mineral oil ingredient of the adhesive, PVP powder of the same was not dissolved into any ingredient of the adhesive but nonhomogeneously dispersed in the warm melt pressure sensitive adhesive.

Referential Example 2

(PVP-Iodine Complex in Hydrophilic Solvent)+Warm Melt Adhesive

In this example, use of a hydrophilic solvent is added, in order to dissolve the PVP powder.

PVP-iodine complex could be dissolved in various hydrophilic solvents including glycols and glycerin, which resulted in homogeneous hydrophilic gels. It was attempted to mix each of these hydrophilic gels with a warm melt pressure sensitive adhesive as described previously. As a result, the hydrophilic gel formed of PVP-iodine complex and hydrophilic solvent was easily separated from the warm melt adhesive.

Referential Example 3

(PVP-Iodine Complex in Hydrophilic Solvent)+Surfactant+Warm Melt Adhesive

Various non-ionic surfactants are added, in order to prevent the separation of hydrophilic gel phase and warm melt adhesion phase and to form a homogeneous and stable iodine-containing warm melt pressure sensitive adhesive composition.

It was found that the hydrophilic gel formed of PVP-iodine complex and hydrophilic solvent could be homogeneously dispersed in the warm melt adhesive as W/O (water in oil) type emulsion, by using a sorbitan ester-type surfactant, such as Span® series and Tween® series commercially available from ICI Co. Particularly, when using Span® 20 (sorbitan monolaurate), the resulting dispersion of the iodine-containing hydrophilic gel into the warm melt adhesive was not only homogeneous and stable, but also transparent.

Working Example 1

Preparation of Iodine-Containing Warm Melt Pressure Sensitive Adhesive Composition Using a non-iodine containing Ecomelt® M1-186 (softening point: 77° C.) from Collano AG, as warm melt pressure sensitive adhesive base, several different warm melt pressure sensitive adhesive compositions, comprising a hydrophilic gel containing PVP-iodine complex, a hydrophilic solvent (PEG300 or glycerin) and a surfactant (Span® 20), were prepared according to the present invention. A few warm melt pressure sensitive adhesive compositions further include sodium iodide. Table 2 shows each formulation of the compositions.

The warm melt pressure sensitive adhesive compositions were prepared as follows. Sodium iodide was dissolved in a hydrophilic solvent (PEG300 or glycerin) within a glass vessel equipped with a seal cap. Then, powdery PVP-iodine complex (from Aldrich Co., iodine content: 11.6 wt. %) was added to and mixed with the solution, and allowed to be dissolved at 90° C. to give a viscous paste mixture. Then, a surfactant Span® 20 was added to and well mixed with the mixture to form a viscous paste of iodine-containing hydrophilic gel. The viscous paste of iodine-containing hydrophilic gel was then mixed with a block of the base warm melt pressure sensitive adhesive Ecomelt® M1-186 in the planetary mixer at 85° C. The iodine-containing warm melt pressure sensitive adhesive compositions prepared in this process was homogenous, and no separation or curing occurred under the storing condition at room temperature, and after cooling, it could be re-melted without any significant change.

TABLE 2

| Composition | Formulation | | | | |
|---|---|---|---|---|---|
| | A | B | C | D | E |
| Ecomelt ® M1-186 | 79.5 | 77.5 | 75.5 | 78.3 | 78.3 |
| Span ® 20 | 1 | 3 | 5 | 1 | 1 |
| PVP-iodine | 9.5 | 9.5 | 9.5 | 9.5 | 9.5 |
| NaI | | | | 1.2 | 1.2 |
| PEG300 | 10 | 10 | 10 | 10 | |
| Glycerin | | | | | 10 |
| | 100 | 100 | 100 | 100 | 100 |

Making and Sterilization of Incise Drape:

Each of the iodine-containing warm melt adhesive compositions A to E, as prepared above, was fed through a standard single screw extruder at 85° C., and from a hot melt coater head of which temperature was set at 85° C., coated on a 50 μm-thick polyester liner identical to that used in comparative example. The coating gap was adjusted to 50 μm. The iodine-containing warm melt adhesive layer coated on the polyester liner, was then laminated with a 25 μm-thick polyester elastic film Hytrel® 4056 identical to that used in comparative example, to form an incise drape.

Each of the incise drapes having each layer of the iodine-containing warm melt adhesive compositions A to E coated thereon, respectively, was then placed into a package bag with moisture barrier pouch identical to that used in comparative example, in a similar manner as in comparative example. The package bag was then heat-sealed. The package pouch containing the incise drape therein was then sterilized by irradiation with Gamma-ray over 25 KGy, in a similar manner as in the comparative example.

Performances of Incise Drape:

Each of the sterilized incise drapes having the layer of each of iodine-containing warm melt adhesive compositions A to E coated thereon, was tested and evaluated on performances as follows: thickness of the coated adhesive layer, iodine content, skin adhesion, iodine sublimation, deformation of the coated adhesive layer, and bleeding of adhesive, in the same manner as described for comparative example. The tests of these performances were conducted, both at the initial state immediately after the Gamma-ray irradiation, and at the state after accelerated aging testing of 9 weeks at 49° C. or 18 weeks at 49° C., which corresponds to one year or two years aging.

Tables 3 to 7 show the results of performances of the incise drapes using the iodine-containing warm melt pressure sensitive adhesive compositions A to E, respectively.

TABLE 3

Performances of Incise Drape with Composition A

| Composition A<br>Span20-1/PVPI/PEG | Initial State | After Aging 1 year | After Aging 2 years |
|---|---|---|---|
| Condition | G-ray 25GKy | 9 Weeks @ 49° C. | 18 Weeks @ 49° C. |
| Thickness (micron) | 35 | 35 | 35 |
| Adhesion (g/inch) | 118 | 102 | 115 |
| Iodine Content (mg/cm$^2$) | 0.0793 | 0.0785 | 0.077 |
| Iodine On Hytrel ® Film | None | None | Trace |
| Sublimation Inside Pouch | None | None | Trace |
| Adhesive Layer Deformation | None | Patterned | Patterned |
| Bleeding of Adhesive | None | None | None |

TABLE 4

Performances of Incise Drape with Composition B

| Composition B<br>Span20-3/PVPI/PEG | Initial State | After Aging 1 year | After Aging 2 years |
|---|---|---|---|
| Condition | G-ray 25GKy | 9 Weeks @ 49° C. | 18 Weeks @ 49° C. |
| Thickness (micron) | 40 | 40 | 40 |
| Adhesion (g/inch) | 48 | 55 | 113 |
| Iodine Content (mg/cm$^2$) | 0.0862 | 0.0844 | 0.084 |
| Iodine On Hytrel ® Film | None | Trace | Oily |
| Sublimation Inside Pouch | None | None | Trace |
| Adhesive Layer Deformation | None | Patterned | Patterned |
| Bleeding of Adhesive | None | None | Much |

TABLE 5

Performances of Incise Drape with Composition C

| Composition C<br>Span20-5/PVPI/PEG | Initial State | After Aging 1 year | After Aging 2 years |
|---|---|---|---|
| Condition | G-ray 25GKy | 9 Weeks @ 49° C. | 18 Weeks @ 49° C. |
| Thickness (micron) | 30 | 30 | 30 |
| Adhesion (g/inch) | 32 | 63 | 85 |
| Iodine Content (mg/cm$^2$) | 0.0727 | 0.0715 | 0.0702 |
| Iodine On Hytrel ® Film | None | Oily | Oily |
| Sublimation Inside Pouch | None | None | None |
| Adhesive Layer Deformation | None | Patterned | Patterned |
| Bleeding of Adhesive | None | Much | Much |

TABLE 6

Performances of Incise Drape with Composition D

| Composition D<br>PEG-BEST-NaI-1.2 | Initial State | After Aging 1 year | After Aging 2 years |
|---|---|---|---|
| Condition | G-ray 25GKy | 9 Weeks @ 49° C. | 18 Weeks @ 49° C. |
| Thickness (micron) | 45 | 45 | 45 |
| Adhesion (g/inch) | 105 | 87 | 148 |
| Iodine Content (mg/cm$^2$) | 0.1306 | 0.1233 | 0.1204 |
| Iodine On Hytrel ® Film Sublimation | None | None | None |
| Inside Pouch | None | None | None |
| Adhesive Layer Deformation | None | None | None |
| Bleeding of Adhesive | None | None | None |

TABLE 7

Performances of Incise Drape with Composition E

| Composition E<br>Glycerine-BEST-NaI-1.2 | Initial State | After Aging 1 year | After Aging 2 years |
|---|---|---|---|
| Condition | G-ray 25GKy | 9 Weeks @ 49° C. | 18 Weeks @ 49° C. |
| Thickness (micron) | 55 | 55 | 55 |
| Adhesion (g/inch) | 139 | 100 | 145 |
| Iodine Content (mg/cm$^2$) | 0.1752 | 0.1747 | 0.1615 |
| Iodine On Hytrel ® Film | None | None | None |
| Sublimation Inside Pouch | None | None | None |
| Adhesive Layer Deformation | None | None | None |
| Bleeding of Adhesive | None | None | None |

As seen from these tables, by the hydrophilic gel formed of PVP-iodine complex, the hydrophilic solvent and the surfactant, sublimation of iodine inside the moisture barrier pouch was suppressed, and iodine was stabilized in the pressure sensitive adhesive. But, for some of the incise drapes, a trace amount of iodine was seen on the Hytrel® film that might have sublimed through the thickness of film to the opposite side of film. However, for the incise drapes in which sodium iodide was added, it was found that even such sublimation of iodine on the film was suppressed and iodine was completely and stably preserved in the pressure sensitive.

Addition of the surfactant into the adhesive composition was effective to stably and homogeneously disperse the iodine-containing hydrophilic gel (aqueous phase) into the warm melt pressure sensitive adhesive base (oily phase). However, when the surfactant was added to a high level, it resulted in lowering of adhesive force and bleeding of the surfactant on the Hytrel® film after the aging test.

Due to the warm melt pressure sensitive adhesive base Ecomelt® M1-186 being relatively soft, deformation of the adhesive layer was also seen after the aging test. Also, the adhesive force was found to be somewhat weak.

Working Example 2

Preparation of Iodine-Containing Warm Melt Pressure Sensitive Adhesive Composition Different warm melt pressure sensitive adhesive compositions were prepared, in which the compositions employ alternative warm melt pressure sensitive adhesive bases having relatively higher softening points, as well as changing the surfactant and hydrophilic solvent levels, in order to improve the adhesive layer deformation and to enhance the adhesive force. The employed warm melt pressure sensitive adhesive bases were Ecomelt® M1-193 (softening point: 84° C.) and Ecomelt® M1-328 (softening point: 88° C.), both from Collano AG. Table 8 shows each formulation of the compositions. These warm melt adhesive compositions were prepared in the same method as described for working example 1, except that the temperature of planetary mixer employed was 90° C., because the softening points of these warm melt are 84 and 88° C.

TABLE 8

| Formulation | | | | |
|---|---|---|---|---|
| | Composition | | | |
| | F | G | H | I |
| PVP-iodine | 9.5 | 9.5 | 9.5 | 9.5 |
| NaI | 1.2 | 1.2 | 1.2 | 1.2 |
| PEG300 | 20 | 20 | 10 | 8 |
| Span® 20 | 1 | 1 | 0.5 | 0.3 |
| Ecomelt® M1-328 | | 68.3 | | |
| Ecomelt® M1-193 | 68.3 | | 78.8 | 81 |
| | 100 | 100 | 100 | 100 |

Making and Sterilization of Incise Drape:

Each of the iodine-containing warm melt adhesive compositions F to I, as prepared above, was fed through a standard single screw extruder at 90° C., and from a hot melt coater head of which temperature was set at 90° C., coated on a 50 μm-thick polyester liner identical to that used in comparative example. The coating gap was adjusted to 50 μm. The iodine-containing warm melt adhesive layer coated on the polyester liner, was then laminated with a 25 μm-thick polyester elastic film Hytrel® 4056 identical to that used in comparative example, to form an incise drape film.

Each of the incise drape films having each layer of the iodine-containing warm melt adhesive compositions F to I coated thereon, respectively, was then placed into a package bag with moisture barrier pouch identical to that used in comparative example, in a similar manner as in comparative example. The package bag was then heat-sealed. The package pouch containing the incise drape therein was then sterilized by irradiation with Gamma-ray over 25 KGy, in a similar manner as in comparative example.

Performances of Incise Drape:

Each of the sterilized incise drapes having the layer of each of iodine-containing warm melt adhesive compositions F to I coated thereon, was tested and evaluated, in the same manner as described for comparative example and working example 1. The tests of these performances were conducted, both at the initial state immediately after the Gamma-ray irradiation, and at the state after accelerated aging testing of 9 weeks at 49° C. corresponding to one year aging.

The results of performances at the initial states of the incise drapes using the iodine-containing warm melt pressure sensitive adhesive compositions F to I, are summarized in Table 9.

As seen from the above table, for the incise drapes (with compositions H and I) in which reduced contents of the hydrophilic solvent (PEG300) and the surfactant (Span® 20) were used, a high and reliable level of adhesive force greater than or equal to 150 g/inch was attained. For all the incise drapes after aging testing of 9 weeks at 49° C., relatively less deformation of adhesive layer was seen, and particularly for the incise drape with composition G employing Ecomelt® M1-328 (softening point: 88° C.), there were little deformation. It was found that use of a warm melt adhesive base having a higher softening point was effective to improve the deformation of adhesive layer.

Example 3

Although the polyester elastic film used to make the incise drapes in the above examples was moisture vapor permeable, the layer of warm melt adhesive containing hydrophilic iodine gel was relatively less moisture vapor permeable. If an incise drape film with an adhesive layer having low moisture vapor permeability is applied to the human skin, the adhesive force of the adhesive will be lowered due to inefficiency of letting out the moisture vapors transpired from the skin. Thus, in order to enhance the moisture vapor transmission rate (MVTR) of warm melt adhesive layer, an improved incise drape was made in which many holes were formed only through the adhesive layer, in an embossing process as described below. In the embossing process, no hole was formed extending through the elastic film, and the elastic film as a barrier against microorganisms was not broken.

Making of Incise Drape Embossed on its Adhesive Layer:

The iodine-containing warm melt adhesive composition F, as prepared in working example 2, was coated on a 50 μm-thick polyester liner in a similar manner as in working example 2, with the coating gap of 50 μm. The iodine-containing warm melt adhesive layer on the polyester liner was processed with an embossing roll at 25° C. (room temperature), to form a number of holes on the adhesive layer (hole diameter: about 0.2 mm, hole density: about 100 holes/cm$^2$). The warm melt adhesive layer was then laminated with a 25 μm-thick polyester elastic film Hytrel® 4056 in a similar manner as in above comparative and working examples, to form an incise drape having the embossed layer of iodine-containing warm melt adhesive coated thereon. The incise drape was then placed into a package bag, and the package containing the incise drape was heat-sealed and subjected to

TABLE 9

Performances of Incise Drapes with Compositions F-I.

| Initial State | Composition F | Composition G | Composition H | Composition I |
|---|---|---|---|---|
| Condition | G-ray 25GKy | G-ray 25GKy | G-ray 25GKy | G-ray 25GKy |
| Thickness (micron) | 40 | 40 | 50 | 70 |
| Adhesion (g/inch) | 56 | 107 | 171 | 184 |
| Iodine Content (mg/cm$^2$) | 0.1005 | 0.0976 | 0.1108 | 0.1849 |
| Iodine Sublimation   On Hytrel® Film | None | None | None | None |
|    Inside Pouch | None | None | None | None |
| Adhesive Layer Deformation | None | None | None | None |
| Bleeding of Adhesive | None | None | None | None | sterilization by irradiation with Gamma-ray over 25 KGy, in similar manners as in above comparative and working examples.

Moisture Vapor Transmission Rate (MVTR):

Measurement of moisture vapor transmission rate (MVTR) for 24 hours at 37° C.-40% RH was conducted on both the incise drape with the embossed layer of iodine-containing warm melt adhesive (composition F) and the incise drape with the non-embossed layer of warm melt adhesive (composition F) as made in working example 2. The results are shown in Table 10.

TABLE 10

Moisture Vapor Transmission Rate of Incise Drape

| Initial State Composition F | Non-embossed | Embossed |
|---|---|---|
| Condition MVTR, 37° C. - 40% RH | G-ray, 25GKy 56 g/m$^2$/24 h | G-ray, 25Gky 203 g/m$^2$/24 h |

Improvement in moisture vapor transmission rate by embossing on the adhesive layer was confirmed.

Various embodiments according to the present invention have been illustrated for incise drape, but it will be apparent to a person ordinarily skilled in the art that the present invention is applicable to other medical adhesive sheet products as well.

The iodine-containing warm melt pressure sensitive adhesive according to the present invention can be used in a wide variety of applications where it is desired to utilize the antimicrobial efficacy of iodine, and it is useful in applications including, but not limited to, medical, skin and beauty applications. They are particularly useful for medical adhesive sheet products including, for example, surgical drapes such as surgical drapes for incision or incise drapes, surgical tapes, and wound dressings.

The invention claimed is:

1. An iodine-containing hot melt pressure sensitive adhesive composition that is capable of being melted and coated at a temperature not higher than 100° C., comprising:
    (a) an iodine-containing hydrophilic gel, comprising
        (i) polyvinyl pyrrolidone-iodine complex, and
        (ii) a hydrophilic solvent with the polyvinyl pyrrolidone-iodine complex dissolved therein;
    (b) a hot melt pressure adhesive base having a softening point of not higher than 100° C., comprising ingredients that are essentially free of ethylenically and acetylenically unsaturated bonds and non-reactive with iodine, said pressure sensitive adhesive base comprising:
        (i) 15 to 30% by weight of a synthetic rubber consisting of a saturated type thermoplastic elastomer,
        (ii) 20 to 35% by weight of a tackifier that is non-reactive with iodine, and
        (iii) 35 to 50% by weight of a plasticizer that is non-reactive with iodine, based on the total weight of the hot melt pressure adhesive base; and
    (c) 0.1 to 0.5% by weight of a surfactant, based on the total weight of the iodine-containing hot melt pressure sensitive adhesive composition; wherein the surfactant is a sorbitan ester-type surfactant.

2. The iodine-containing hot melt pressure sensitive adhesive composition according to claim 1, wherein said hydrophilic solvent is selected from the group consisting of glycols and glycerin.

3. The iodine-containing hot melt pressure sensitive adhesive composition of claim 1, wherein said hydrophilic solvent is selected from the group consisting of PEG300 and glycerin.

4. The iodine-containing hot melt pressure sensitive adhesive composition according to claim 1, wherein said hot melt pressure adhesive base comprises (i) a synthetic rubber consisting of a saturated type thermoplastic elastomer selected from the group consisting of hydrogenated styrene-ethylene/butylene-styrene block copolymers, hydrogenated styrene-ethylene/propylene-styrene block copolymers, polymer alloys thereof, and blends thereof, (ii) a tackifier selected from C5 based hydrocarbon resins, and (iii) a mineral oil.

5. The iodine-containing hot melt pressure sensitive adhesive composition according to claim 1, wherein said pressure sensitive adhesive composition further comprises an iodide salt that is soluble in said hydrophilic solvent.

6. A medical adhesive sheet product, comprising:
    (a) a sheet substrate; and
    (b) an iodine-containing hot melt pressure sensitive adhesive composition as defined in claim 1, coated on said sheet substrate.

7. The medical adhesive sheet product according to claim 6, wherein one or more holes are formed only through a layer of said pressure sensitive adhesive composition coated on said sheet substrate, without any hole formed through said sheet substrate, by embossing on the layer of said pressure sensitive adhesive composition.

8. The medical adhesive sheet product according to claim 6, wherein said medical adhesive sheet product is a surgical drape for incision.

9. A medical adhesive sheet product of claim 6, wherein the hydrophilic solvent is selected from the group consisting of glycols and glycerin.

10. A medical adhesive sheet product of claim 6, wherein the hydrophilic solvent is selected from the group consisting of PEG300 and glycerin.

11. A medical adhesive sheet product of claim 6, wherein the hot melt pressure adhesive base comprises (i) a synthetic rubber consisting of a saturated type thermoplastic elastomer selected from the group consisting of hydrogenated styrene-ethylene/butylene-styrene block copolymers, hydrogenated styrene-ethylene/propylene-styrene block copolymers, polymer alloys thereof, and blends thereof, (ii) a tackifier selected from C5 based hydrocarbon resins, and (iii) a mineral oil.

12. A medical adhesive sheet product of claim 6, wherein the pressure sensitive adhesive composition further comprises an iodide salt that is soluble in said hydrophilic solvent.

13. An iodine-containing hot melt pressure sensitive adhesive composition that is capable of being melted and coated at a temperature not higher than 100° C., comprising:
    (a) an iodine-containing hydrophilic gel, comprising
        (i) polyvinyl pyrrolidone-iodine complex, and
        (ii) a hydrophilic solvent with the polyvinyl pyrrolidone-iodine complex dissolved therein;
    (b) a hot melt pressure adhesive base having a softening point of not higher than 100° C., comprising
        (i) 15 to 30% by weight of a synthetic rubber consisting of a saturated type thermoplastic elastomer,
        (ii) 20 to 35% by weight of a tackifier that is non-reactive with iodine, and
        (iii) 35 to 50% by weight of a plasticizer that is non-reactive with iodine, based on the total weight of the hot melt pressure adhesive base;
    (c) 0.1 to 0.5% by weight of a surfactant, based on the total weight of the iodine-containing hot melt pressure sensitive adhesive composition; wherein the surfactant is a sorbitan ester-type surfactant; and
    (d) an iodide salt that is soluble in said hydrophilic solvent.

14. A method of making a medical adhesive sheet product, the method comprising:

providing a sheet substrate; and hot melt coating on said sheet substrate an iodine-containing hot melt pressure sensitive adhesive composition at a temperature not higher than 100° C., wherein said iodine-containing hot melt pressure sensitive adhesive composition comprises:

(a) an iodine-containing hydrophilic gel, comprising
   (i) polyvinyl pyrrolidone-iodine complex, and
   (ii) a hydrophilic solvent with the polyvinyl pyrrolidone-iodine complex dissolved therein;

(b) a hot melt pressure adhesive base having a softening point of not higher than 100° C., comprising ingredients that are essentially free of ethylenically and acetylenically unsaturated bonds and non-reactive with iodine, said pressure sensitive adhesive base comprising:
   (i) 15 to 30% by weight of a synthetic rubber consisting of a saturated type thermoplastic elastomer,
   (ii) 20 to 35% by weight of a tackifier that is non-reactive with iodine, and
   (iii) 35 to 50% by weight of a plasticizer that is non-reactive with iodine, based on the total weight of the hot melt pressure adhesive base; and (c) 0.1 to 0.5% by weight of a surfactant, based on the total weight of the iodine-containing hot melt pressure sensitive adhesive composition; wherein the surfactant is a sorbitan ester-type surfactant.

* * * * *

UNITED STATES PATENT AND TRADEMARK OFFICE
CERTIFICATE OF CORRECTION

PATENT NO. : 7,871,699 B2  
APPLICATION NO. : 11/596151  
DATED : January 18, 2011  
INVENTOR(S) : Shunsuke Takaki Page 1 of 1

It is certified that error appears in the above-identified patent and that said Letters Patent is hereby corrected as shown below:

Cover page, Column 1 (Title), Line 4: Delete "100C," and insert -- 100°C, --, therefor Column 1, Line 4: Delete "100C," and insert -- 100°C, --, therefor Signed and Sealed this  
Twenty-sixth Day of April, 2011

David J. Kappos  
*Director of the United States Patent and Trademark Office*